US006687522B2

(12) United States Patent
Tamada

(10) Patent No.: US 6,687,522 B2
(45) Date of Patent: *Feb. 3, 2004

(54) DEVICE FOR SAMPLE OF SUBSTANCES USING ALTERNATING POLARITY

(75) Inventor: Janet Tamada, Belmont, CA (US)

(73) Assignee: Cygnus, Inc., Redwood City, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 09/893,916

(22) Filed: Jun. 28, 2001

(65) Prior Publication Data

US 2002/0002328 A1 Jan. 3, 2002

Related U.S. Application Data

(63) Continuation of application No. 09/430,914, filed on Nov. 1, 1999, now Pat. No. 6,298,254, which is a continuation of application No. 08/968,700, filed on Nov. 10, 1997, now Pat. No. 6,023,629, which is a continuation of application No. 08/265,844, filed on Jun. 24, 1994, now Pat. No. 5,771,890.

(51) Int. Cl.[7] ................................................. A61B 5/05
(52) U.S. Cl. ....................... 600/347; 604/20; 600/396
(58) Field of Search ............................ 600/309, 345, 600/347, 348, 354, 355, 357, 372, 382, 384, 356, 397; 604/20; 204/153.12

(56) References Cited

U.S. PATENT DOCUMENTS

| | | | |
|---|---|---|---|
| 3,686,088 A | 8/1972 | Kashii | |
| 4,256,978 A | 3/1981 | Pinckaers | |
| 4,301,794 A | 11/1981 | Tapper | |

(List continued on next page.)

FOREIGN PATENT DOCUMENTS

| | | |
|---|---|---|
| AU | 8818506 | 6/1988 |
| AU | 652135 | 6/1991 |
| EP | 0 230 153 | 7/1987 |
| EP | 0 230 749 | 8/1987 |
| EP | 0 304 304 | 2/1989 |
| WO | WO 92/07619 | 5/1992 |
| WO | WO 92/10234 | 6/1992 |

OTHER PUBLICATIONS

Dialog Patent Database Abstract of German Patent No. DE 3,812,537 (Oct. 26, 1989).
Dialog Patent Database Abstract of Japanese Patent No. 4224770 (Aug. 14, 1992).
Dialog Patent Database Abstract of Japanese Patent No. 3045272 (Feb. 26, 1991).

(List continued on next page.)

Primary Examiner—Eric F. Winakur
(74) Attorney, Agent, or Firm—Barbara G. McClung; Cary R. Fabian

(57) ABSTRACT

A method for sampling of a substance from a subject is provided, which comprises placing one or more sampling chambers on a collection site on a tissue surface on the subject; conducting electric current through the tissue to extract a substance from the subject in a first direction in one or more sampling chambers that functions alternatively as both an anode and cathode during the course of the method; reversing the polarity to cause direct current to flow in second direction opposite the first direction; and analyzing the sampling chamber or chambers for the concentration of a substance or a substance metabolite. There is also provided a device for sampling of a substance from an organism on continuously or intermittently using alternating polarity method based on the application of low intensity electric fields of alternating polarity across the skin (iontophoresis) to enhance the transport of a substance (such as glucose, lactic acid, pyruvic acid, and the like) from body tissues to a sampling chamber. The device comprises an electrical power supply; a transdermal system that contains one or more sampling chambers that function as both anode and cathode during the course of sampling; a means to alternates or reverses the polarity during the iontophoretic sampling; and means for analyzing for the concentration of a substance or a substance metabolite.

32 Claims, 11 Drawing Sheets

U.S. PATENT DOCUMENTS

| | | |
|---|---|---|
| 4,325,367 A | 4/1982 | Tapper |
| 4,340,047 A | 7/1982 | Tapper et al. |
| 4,406,658 A | 9/1983 | Lattin et al. |
| 4,477,971 A | 10/1984 | Jacobsen et al. |
| 4,633,879 A | 1/1987 | Ong |
| 4,640,689 A | 2/1987 | Sibalis |
| 4,702,732 A | 10/1987 | Powers et al. |
| 4,722,761 A | 2/1988 | Cartmell et al. |
| 4,725,263 A | 2/1988 | McNichols et al. |
| 4,731,049 A | 3/1988 | Parsi |
| 4,752,285 A | 6/1988 | Petelenz et al. |
| 4,786,278 A | 11/1988 | Masaki |
| 4,792,702 A | 12/1988 | Masaki |
| 4,822,334 A | 4/1989 | Tapper |
| 5,006,108 A | 4/1991 | LaPrade |
| 5,013,293 A | 5/1991 | Sibalis |
| 5,036,861 A | 8/1991 | Sembrowich et al. |
| 5,076,273 A | 12/1991 | Schoendorfer et al. |
| 5,133,351 A | 7/1992 | Masaki |
| 5,135,480 A | 8/1992 | Bannon et al. |
| 5,139,023 A | 8/1992 | Stanley et al. |
| 5,140,985 A | 8/1992 | Schroeder et al. |
| 5,224,927 A | 7/1993 | Tapper |
| 5,279,543 A | 1/1994 | Glikfeld et al. |
| 5,291,887 A | 3/1994 | Stanley et al. |
| 5,362,307 A | 11/1994 | Guy et al. |
| 5,735,273 A | 4/1998 | Kurnik et al. |
| 5,771,890 A | 6/1998 | Tamada |
| 5,827,183 A | 10/1998 | Kurnik et al. |
| 5,954,685 A | 9/1999 | Tierney |
| 5,989,409 A | 11/1999 | Kurnik et al. |
| 6,023,629 A | 2/2000 | Tamada |
| 6,139,718 A | 10/2000 | Kurnik et al. |
| 6,141,573 A | 10/2000 | Kurnik et al. |
| 6,144,869 A | 11/2000 | Berner et al. |
| 6,180,416 B1 | 1/2001 | Kurnik et al. |
| D437,603 S | 2/2001 | Liu |
| D438,807 S | 3/2001 | Liu |
| 6,201,979 B1 | 3/2001 | Kurnik et al. |
| 6,233,471 B1 | 5/2001 | Berner et al. |

OTHER PUBLICATIONS

Glikfeld et al., "Noninvasive Sampling of Biological Fluids by Lontophoresis", *Pharm. Res.* (1989) vol. 6, No. 11, pp. 988–990.

Meyerhoff et al., "On Line Continuous Monitoring of Subcutaneous Tissue Glucose in Men by Combining Portable Glucosensor with Microdialysis", *Diabetologia* (1992) vol. 35, pp. 1087–1092.

Garg, et al. "Correlation of Fingerstick Blood Glucose Measurements with GlucoWatch(R) Biographer Glucose Results in Young Subjects with Type 1 Biabetes", Diabetes Care (1999) 22: 1708–1714.

DEVICE FOR SAMPLE OF SUBSTANCES USING ALTERNATING POLARITY

CROSS-REFERENCE TO RELATED APPLICATIONS

This application is a continuation of U.S. application Ser. No. 09/430,914. filed Nov. 1, 1999. now U.S. Pat. No. 6,298,254, which is a continuation of U.S. application Ser. No. 08/968,700, filed on Nov. 10, 1997, now U.S. Pat. No. 6,023,629, which is a continuation of U.S. application Ser. No. 08/265,844, filed Jun. 24, 1994, now U.S. Pat. No. 5,771,890, from which applications priority is claimed pursuant to 35 U.S.C. §120 and which applications are incorporated herein by reference in their entireties.

FIELD OF THE INVENTION

This invention relates to a device and method for sampling of substances across tissue using electrical energy of alternating polarity.

BACKGROUND OF THE INVENTION

Iontophoresis is employed for therapeutic topical treatment of humans or other organisms. Glikfeld et al., U.S. Pat. No. 5,279,543, describes the use of iontophoresis to non-invasively sample a substance through skin into a receptor chamber on the skin surface. The Glikfeld device consists of two chambers, each containing an electrically conductive medium, which medium is in electrical contact with the skin. A positive electrode (anode) is disposed in one chamber, and a negative electrode (cathode) is disposed in the other. The two chambers are separated by an electrically insulating material. In use, a constant or pulsed current is generated by a power source between the electrodes through the skin. The direction of current flow never changes during sampling. Glikfeld does not correlate the collected substance levels with blood substance levels and does not address any problems associated with long term transdermal monitoring of a substance.

The Lattin and Spevak U.S. Pat. No. 4,406,658, Tapper U.S. Pat. Nos. 4,301,794, 4,340,047 and 5,224,927, Masaki U.S. Pat. No. 4,786,278, Masaki U.S. Pat. No. 4,792,702 and Masaki European Patent No. 230,153 describe the iontophoretic delivery of a substance across tissue. In addition, these publications describe operation methods in which the polarity of the applied electrical energy is reversed during delivery. None of these publications addresses extraction of substances from tissue or any of the problems associated with such extraction.

The Tapper '794 and '047 patents address the irritation caused by iontophoretic delivery of ionized molecules through skin. In the Tapper apparatus, all delivery occurs at a single electrode. Tapper determined that the irritation can be eliminated if the polarity of the applied current is reversed for equal periods. A complete and equal polarity reversal eliminates the molecule delivery, however. Tapper compromises by providing for a shorter period for the reverse direction and a longer period for the forward (substance delivery) direction.

The Tapper '927 patent discloses an apparatus that iontophoretically delivers a substance into the patient's skin from two source reservoirs, each attached to an electrode. The electrodes are connected to an AC power source having a frequency in the range of 0.0027–10 Hz. Use of an AC power source minimizes the build-up of irritating chemicals at positive and negative electrodes (e.g., HCl and $H_2O_2$, respectively). Providing a source reservoir at both electrodes permits delivery from one of the reservoirs in each phase of the AC signal, thereby eliminating the drawback of using a single source reservoir noted in the earlier Tapper patents.

Some alternating polarity methods for drug delivery, such as in the Tapper '927 patent focus on prevention of pH changes. For many electrode systems, water hydrolysis upon the application of current causes the pH to dramatically decrease at the anode and increase at the cathode. This can cause skin irritation. Furthermore, the pH changes in the drug donor electrodes can reduce the amount of ionized drug relative to non-ionized drug in the donor depending on the pKa of the drug. These patents propose switching between the anode and cathode to prevent these pH changes, reducing irritation and possibly increasing drug flux, especially of ionizable drugs.

The Lattin and Spevak '658 patent allows for delivery from both electrodes, thus doubling the potential delivery area. For drug delivery applications, more area means more deliverable drug per application of a single device. However, for iontophoretic sampling applications, there is no advantage to doubling the area because total delivery is not an important factor. The amount that is sampled per area is more important because it is the substance concentration that is to be measured, not the total substance amount.

The Masaki patents disclose a device and a switch which can iontophorese both anions and cations by switching the polarity of the two electrodes during the treatment cycle. In the Masaki '702 patent, the cations and anions come from a single source reservoir attached to one electrode. The other two patents do not disclose where the cation and anion sources are located. In any event, these patents teach nothing about iontophoretic sampling from skin into a reservoir.

Sibalis U.S. Pat. No. 5,013,293 describes an "electrophoretic" drug delivery system in which a drug is delivered from a reservoir into the patient's skin under the action of current applied to two electrodes, one of which is attached to the reservoir. The polarity of the current may be alternated periodically to control the amount of drug delivered. Sibalis does not disclose the use of iontophoresis for removing a substance from a patient's tissue.

LaPrade U.S. Pat. No. 5,006,108 discloses alternating polarity for the delivery of drugs in which the surface area of both electrodes (each alternating between being the anode and cathode) is available to deliver the drug. The LaPrade disclosure does not suggest that: (1) a single electrode may be used as a collector during iontophoretic extraction, with that electrode alternating between being an anode and a cathode; (2) two electrodes may act alternatively as anode and cathode during iontophoretic extraction, or (3) iontophoresis can be used generally for removing substances from tissue.

Some alternating polarity patents for drug delivery, such as the above LaPrade and Lattin patents, focus on increasing drug dosage with the same size patch. The principle is that the available surface area for delivery is larger for alternating polarity because each electrode can be both an anode and a cathode, rather than one electrode being the "active" electrode and the other electrode taking up space, but not helping drug delivery, as the "indifferent" electrode. This results in more drug delivery, but would not aid in extraction where substance flux, not "total" substance delivered, is the critical factor.

Teijin LTD, Japanese patent publication 4224770, discloses an apparatus with electrodes for attachment to skin which has hydrous medium for electrically contacting the electrodes, containing medically active agent to be absorbed through the skin, and current polarity switching means. Apparently, this patent is designed to reduce pH deviation.

Teijin LTD, Japanese patent publication 3045272, discloses a compact iontophoresis device which comprises electrodes containing medicine and applied with high frequency AC for percutaneous administration and with the objective of reducing skin irritation.

SUMMARY OF THE INVENTION

In the area of in vivo extraction of substances from tissue, correlation between measured concentrations of extracted substances must be correlated with levels of the substance within the patient's tissue and/or blood stream. For example, studies have shown a need for a virtual continuous glucose monitor, which could potentially signal a diabetic of dangerously low or high blood sugar levels. The greater the flux of the extracted substance from the tissue into the substance collector, the greater the accuracy with which the measured flux can be correlated with the concentration of the substance within the tissue and/or blood stream. What is needed, therefore, is a way to decrease the difference between the measured concentration of the extracted substance and the concentration of the substance within the tissue and/or blood.

Standard iontophoretic electrodes generally involve either water hydrolysis, which can cause undesirable pH changes, or a silver/silver chloride reaction in which silver chloride is converted to silver at the cathode, and silver is converted to silver chloride at the anode. For either of these systems, long term application of current can be a problem due to the eventual depletion of the reactants. What is needed, therefore, is a iontophoretic sampling system and method that avoids this problem.

This invention is directed to a device and method for sampling of a substance using electrical energy applied in alternating polarity. Alternating the polarity allows the reactions, such as silver/silver chloride reaction or the water hydrolysis reaction, to cycle back and forth, potentially lengthening the time that a particular electrode could be used. In the non-invasive sampling method of the invention the pertinent parameter is the extraction of the desired substance per unit surface area (flux), not the total extraction.

The invention includes a method for sampling of a substance from a subject, which comprises (a) placing one or more sampling chambers on a collection site on a tissue surface of a subject;

(b) conducting electrical current through the tissue in a first polarity to extract a substance from the subject into one or more sampling chambers;

(c) reversing the polarity of the electrical current during the course of the method (i.e., changing an anode to a cathode and a cathode to an anode); and (d) analyzing the sampling chamber or chambers for the concentration of the substance or a substance metabolite.

The invention also includes a sampling device comprising (a) an electrical power supply means;

(b) a transdermal system that contains one or more sampling chambers for receiving a sample that function as both anode and cathode during the course of iontophoretic sampling;

(c) means for reversing the polarity of the power source during the iontophoretic sampling; and (d) means for analyzing the sampling chamber or chambers for the concentration of the substance or a substance metabolite.

The invention also includes a substance monitor comprising:

first and second substance sampling chambers each containing substance collection medium selected from the group consisting of water, saline solutions, buffer solutions, and polyols;

a power supply means having a positive connector and a negative connector;

conductors and a switch electrically connecting the first and second sampling chambers to the power supply means positive connector and the power supply means negative connector, the switch having a first position in which the first sampling chamber is electrically connected to the positive connector and the second sampling chamber is electrically connected to the negative connector and a second position in which the second sampling chamber is electrically connected to the positive connector and the first sampling chamber is electrically connected to the negative connector.

The reversal of polarity during the sampling method of the invention has advantages over a prior standard iontophoresis method (non-alternating direct or intermittent current application) including: (1) there is unexpected enhancement of the correlation between blood and iontophoretically extracted samples under the alternating polarity method of the invention as compared to a non-alternating polarity protocol, (2) there is a particularly unexpected normalized flux rate increase over the use of direct current, and (3) the alternating polarity method of the invention enables continuous or intermittent application of current for Ag/AgCl or other electrodes without depletion of the AgCl plating or pH variations which occur for non-alternating systems.

The ionization state of the substance of the drug delivery materials of the prior art were dictated by the pH of the donor solutions. However, in the alternating polarity sampling method of the invention, the ionization state of the extracted substance does not rely on the pH of the donor chamber; rather, the ionization state of the extracted species going from the body to the top of the skin is dictated by the pH of the body, which is relatively constant.

The alternating polarity sampling method and device of the invention preferably uses low frequencies of about 0.1 Hz (one switch every 10 seconds) to about 1 switch every hour. This is in contrast to the drug delivery of the prior art, such as Tapper '794 and Masaki '351 which disclose that in a desire to reduce skin irritation, rapid, high frequency pulsing, of either the same or alternating polarity, reduces skin irritation caused by iontophoresis.

These advantages are surprising considering the non-invasive nature of the method and device which produces these advantages when transporting substances that are beneath the skin to a collection reservoir on top of the skin while no part of the device penetrates into or beneath the skin.

DETAILED DESCRIPTION OF THE DRAWINGS

Figure 14:
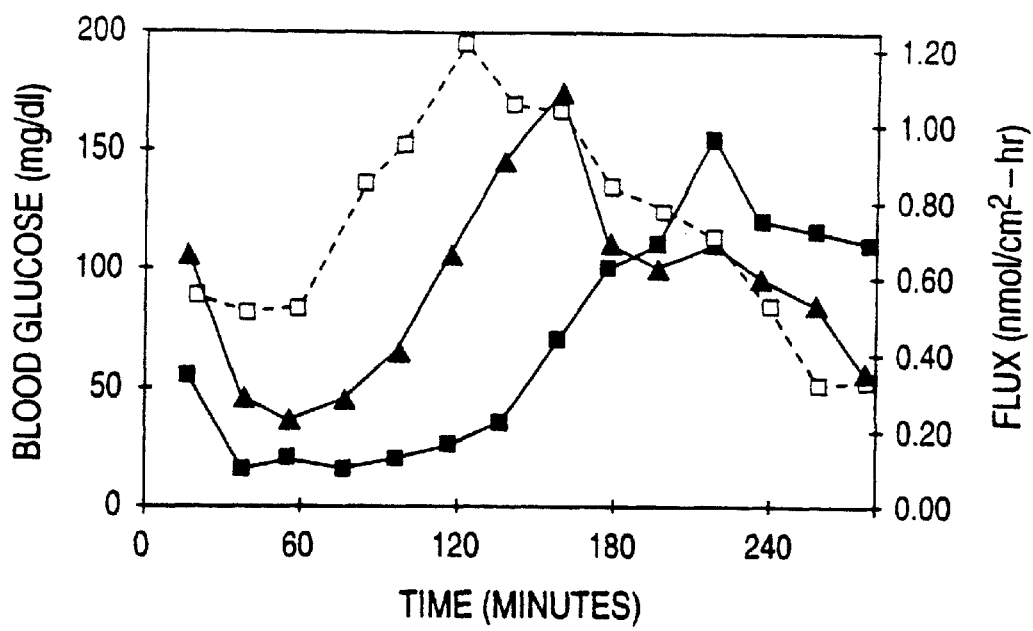

FIG. 14, subject D, right arm, demonstrates that the standard DC protocol did not show this oscillation.

Figure 15:
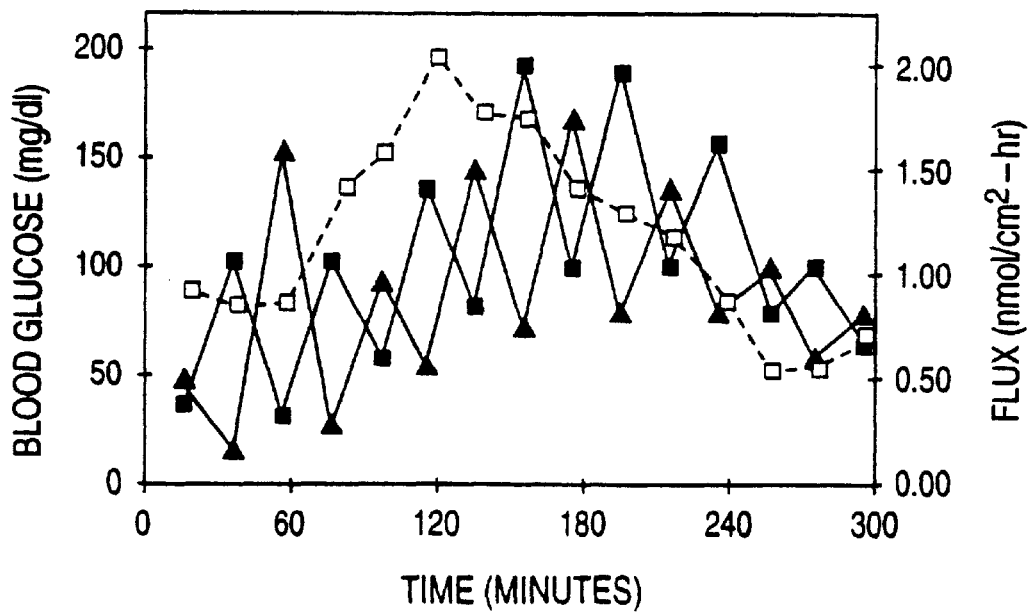

FIG. 15, Subject D, left arm, showed sharp oscillation in the iontophoretically extracted glucose at the cathode as the physical site of extraction was switched from one extraction site on the forearm to the other during the alternating polarity protocol.

Figure 16:
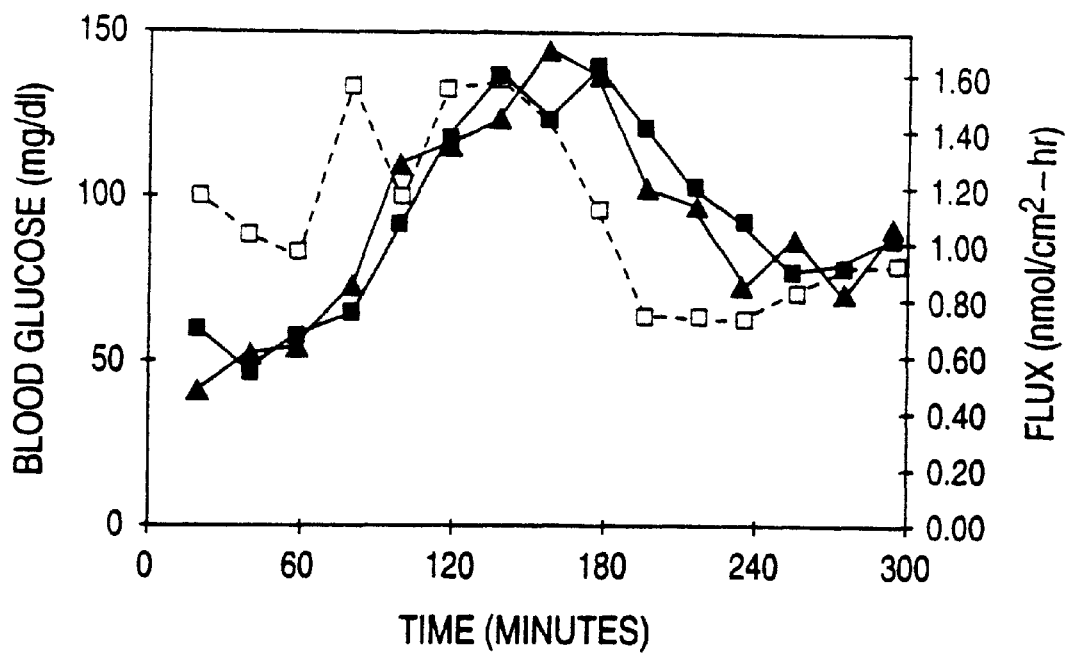

FIG. 16, subject B, left arm, shows that the oscillatory behavior is smoothed out by alternating the polarity every 7.5 minutes rather than every 15 minutes.

Figure 17:
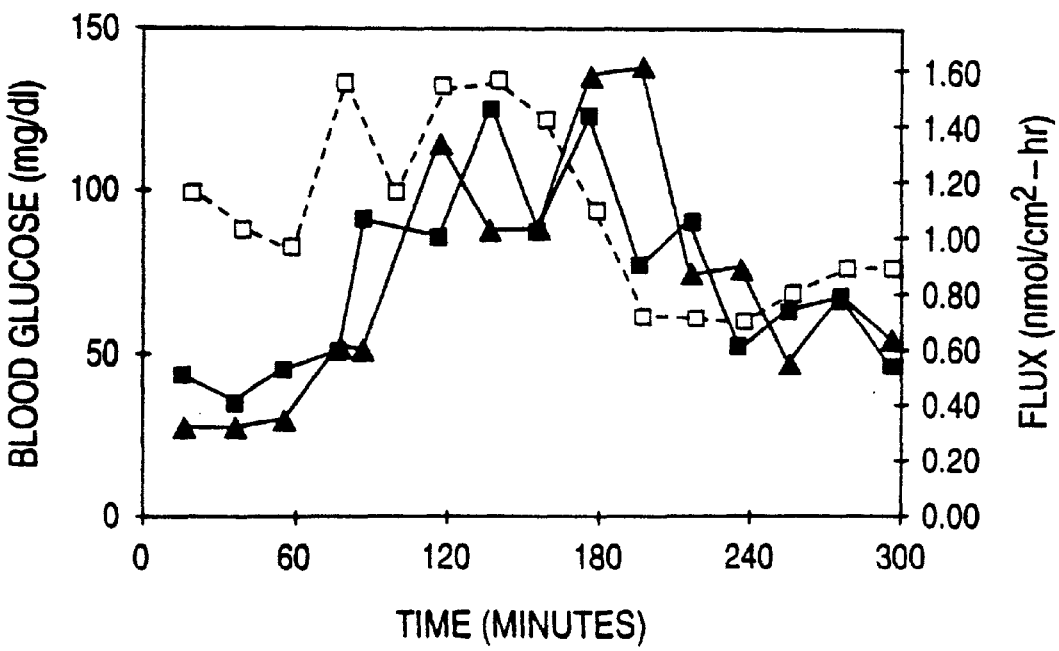

FIG. 17, subject B, right arm, shows the oscillatory behavior, similar to that observed in Example 4, for the 15-minute alternating polarity protocol.

Figure 2:
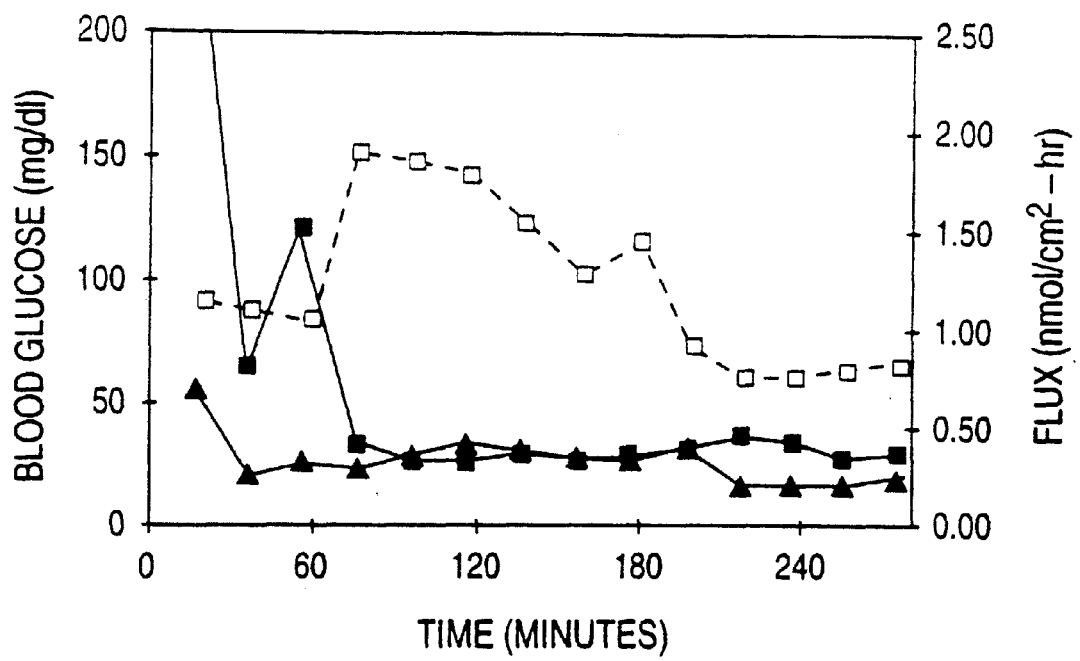
FIG. 2 is a graph of the results of a blood oral glucose tolerance glucose monitoring experiment on subject A, right arm, using a standard protocol.
Figure 18:
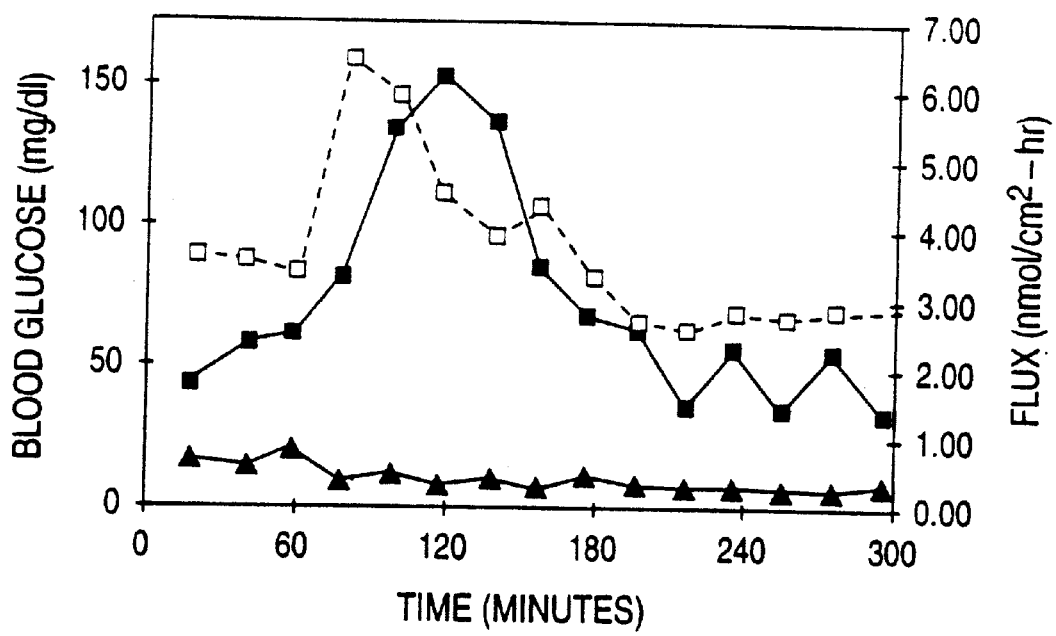

FIG. 18, subject A, right arm, demonstrates the dramatic enhancement in flux at the cathode for a direct current protocol using pH 8.2 sodium bicarbonate buffered saline solution compared to FIG. 2 for the same Subject B using 0.45% sodium chloride solution.

Figure 3:
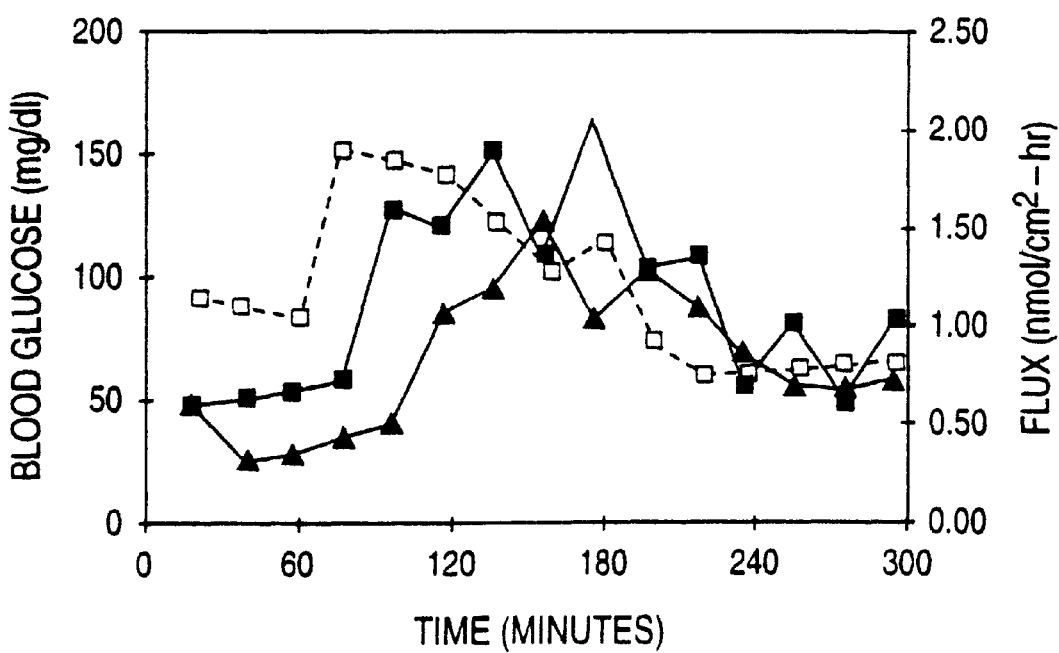
FIG. 3 is a graph of the results of a blood oral glucose tolerance glucose monitoring experiment on subject A, left arm, using an alternating protocol.
Figure 19:
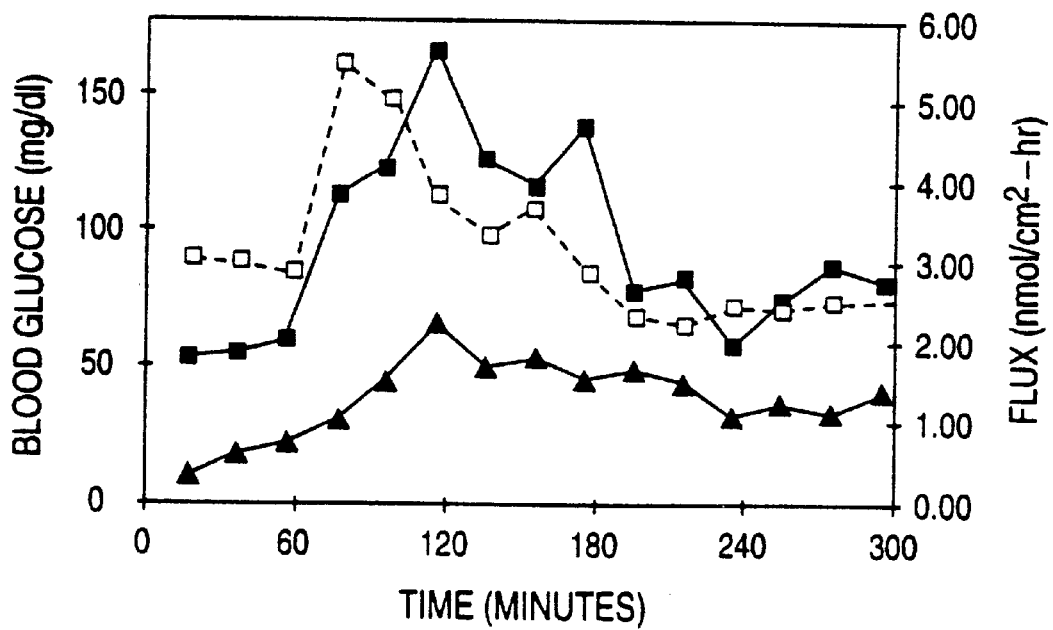

FIG. 19, subject A, left arm, demonstrates the dramatic enhancement of flux at the cathode for the alternating polarity protocol using pH 8.2 sodium bicarbonate buffered saline solution compared to FIG. 3 for the same Subject B using 0.45% sodium chloride solution.

DETAILED DESCRIPTION OF THE INVENTION

Unless defined otherwise all technical and scientific terms used herein have the same meaning as commonly understood by one of ordinary skill in art to which this invention is directed. Although any methods and materials similar or equivalent to those described herein can be used in the practice or testing of this invention, the preferred methods and materials are now described.

All patents and publications cited herein are incorporated herein by reference for the purpose of disclosing and describing information in connection with which the patents and publications are cited.

By "conducting electrical current through the tissue to extract the substance into one or more sampling chambers/ collection reservoirs" is meant applying electrical energy of sufficient strength and duration to the tissue surface of a subject in order to transport a substance or a metabolite from beneath the skin at a collection site on the surface of the tissue into a defined collection area. This includes the method known as iontophoresis. "Iontophoresis" as used herein means a method of treatment to drive uncharged non-ionic materials and positive or negative ions out of an organism through tissue. In conventional iontophoresis two electrodes are placed in contact with the tissue. One or both of the electrodes is in a sampling chamber/collection reservoir to collect the substance extracted and a voltage is applied between the two electrodes. The sampling chamber/ collection reservoir is provided at the tissue surface to serve as a collector of material transported.

As used herein "sampling" or "monitoring" means the extraction of a substance from an organism through the tissue. The tissue or skin can be natural or artificial tissue and can be of plant or animal nature, such as natural or artificial skin, blood vessel tissue, intestinal tissue, mucosal epithelial tissue, and the like. The term "artificial" as used herein means an aggregation of cells of monolayer thickness or greater which are grown or cultured in vivo or in vitro and which function as a tissue of an organism but are not actually derived, or excised, from a pre-existing source or host. The subject/patient or host organism can include warm-blooded animals and is, particularly, a mammal, such as rats, mice, pigs, dogs, cats, cattle, sheep, horses, and especially a human being. When the tissue is human skin, the tissue surface is the stratum corneum surface, mucosal tissue as in the oral, nasal, or vaginal cavity or the like.

There is a need to sample and quantify or qualify bioactive substances, such as glucose or a glucose metabolite, in a body, such as in the blood, for example, to monitor the presence of a endogenous biochemical for the purpose of diabetes diagnosis and treatment, forensic evaluation, or to follow, and preferably optimize the blood level of an administered drug during a chemotherapeutic regimen. This preferably needs to be done without the invasive withdrawal of blood by a needle into a collection reservoir/container. In some applications, e.g. diabetes treatment, for maximum benefit, sampling and quantification also should be performed substantially continuously and the measured substance values need to correlate actual blood substance levels.

Substances that can be sampled from an organism include anything found in the system of an animal, including a wide variety of body materials intended for diagnosis, such as natural and therapeutically introduced metabolites, hormones, amino acids, peptides and proteins, electrolytes, metal ions, suspected drugs of abuse, enzymes, tranquilizers, anesthetics, muscle relaxants, sedatives, antipsychotic agents, antidepressants, antianxiety agents, small drug molecules, and the like. Non-limiting representative examples of such materials include glucose, lactic acid, pyruvic acid, alcohols, fatty acids, glycols, thyroxine, estrogen, testosterone, theobromine, sucrose, galactose, uric acid, alpha amylase, choline, L-lysine, sodium, potassium, copper, iron, magnesium, calcium, zinc, potassium, citrate, morphine, morphine sulfate, heroin, insulin, steroids, neomycin, nitrofurazone, beta-methasone, clonidine and clonidine HCl, acetic acid, alkaloids, acetaminophen, and amino acids. More than one substance can be sampled at one time. In one embodiment, the invention includes a continuous monitoring of the levels of glucose or glucose metabolite from the body.

According to one embodiment, the invention is useful in continuous monitoring of levels of a substance (glucose) or a substance (glucose) metabolite, e.g., lactic acid, from the body. The method can also be used for measurement of blood substance (glucose) levels in either a semi-continuous or a single measurement method. The method can be practiced by a device that provides electrodes or other means for applying electric current to the tissue at the collection site; one or more collection reservoirs or sampling chambers to receive the substance (glucose); and a substance concentration measurement system. A continuous glucose monitoring method and apparatus according to this embodiment is described in a patent application Ser. No. 08/265,048 entitled "Continuous Transdermal Glucose Monitoring Method and Apparatus" filed concurrently with this application and assigned to the assignee of this application, the disclosure of which is incorporated herein by reference. A preferred embodiment of the method and apparatus are described in more detail below.

The method and device of the invention are useful in providing non-invasive monitoring of the levels of a substance, such as glucose or a glucose metabolite, from the body. For example, the method and device can be used for the measurement of blood glucose levels in a diabetic subject in either a semi-continuous or a single measurement method. The method can be practiced with a device of the invention based on the application of low intensity electric fields of alternating polarity across the tissue/skin (iontophoresis) to enhance the transport of molecules, such as glucose, lactic acid, pyruvic acid, and the like, from body tissues to one or more collection reservoirs/sampling chambers.

According to the method of the invention, a collection reservoir is placed at a collection site on a tissue surface of the patient, for example, on the stratum corneum of the patient's skin or on the mucosal epithelium. Electrical energy is applied to the tissue at the collection site to move the substance from the tissue into the collection reservoir. The collection reservoir is analyzed periodically to measure the substance level concentration therein, and this measured concentration value is preferably correlated with the patient's blood substance level. The steps are repeated to monitor the patient's blood substance level, preferably substantially continuously, and to track changes in the patient's blood substance level.

In a preferred embodiment of the method, two electrodes provide the electrical energy to the tissue at the collection site or sites. Two collection reservoirs are provided, one at or near each electrode. The applied electrical current is preferably in the range of about 0.01 to about 2 mA/cm$^2$. In applying the electrical energy, the polarity of the electrodes is alternated, e.g., at a rate in the range of about 0.1 Hz (one switch every 10 seconds) to about 1 switch every hour, so that each electrode is alternately a cathode or an anode. The substance in question (e.g., glucose) is collected in both reservoirs, but is most preferably measured in the reservoir acting as the cathode. In other words, the reservoir in which glucose concentration is monitored alternates as the polarity of the electrodes alternates. The actual frequency of the polarity switch may need to be optimized for the substance being extracted and measured.

The reversal of polarity during sampling has advantages, including: (1) an unexpected enhancement of the correlation between blood and/or tissue concentrations and iontophoretically extracted samples under the alternating polarity method of the invention as compared to a non-alternating polarity protocol, (2) a particularly unexpected increase in the normalized flux rate, and (3) the avoidance of depletion of the AgCl plating on AgCl electrodes or pH variations which occur for non-alternating systems.

The polarity switching can be manual or automatic. The polarity switching can be of any frequency, especially at frequencies between about 1 cycle per 20 seconds to about 1 cycle per 4 hours, preferably between about 1 cycle per 20 seconds to about 1 cycle per 2 hours, or more preferably between about 1 cycle per minute to about 1 cycle per 2 hours, or between about 1 cycle per 10 minutes to about 1 cycle per hour, and especially is about 1 cycle per half hour. By cycle is meant one interval of current in each direction. The application of electrical energy in a given cycle may cease during analysis of the collection medium.

In the preferred method, part or all of the collection medium is extracted from the collection reservoir and analyzed for concentration of the substance in question. One preferred analysis method is high pressure liquid chromatography (HPLC), although other analysis methods may be used such as pulsed amperometric detection.

To provide useful information regarding concentration levels of the substance in the patient's blood and/or tissue, the substance concentrations detected in the collection medium must be correlated with the tissue and/or blood levels. Concentration in the collection medium is computed in flux terms, such as nmoles/cm$^2$·hr. This information must be translated into corresponding values (expressed, e.g., in terms of mg/dl for blood substance concentrations).

For example, correlation between blood glucose concentration and measure glucose flux may be expressed in terms of four variables: the time lag between blood glucose concentration values and measured glucose flux values; linear drift over time of the measured glucose flux values; and the slope and intercept (i.e., the low-end blood glucose value below which no glucose flux is detected) of a line relating time lag and drift-corrected glucose flux data to blood glucose concentration. Correlation between measured glucose flux and actual blood glucose concentration is accomplished through a calibration procedure which relates blood glucose data and glucose flux data.

Time lag is defined as the constant time shift between blood glucose and glucose flux curves that achieves a best fit in curve shape along the time axis within predefined tolerances. The amount of time shift may be determined manually or automatically with the aid of a computer or other processor using known curve shape comparison algorithms. Time shift is illustrated in FIGS. 8 & 9 and FIGS. 10 & 11.

Drift is defined as the linear change with time of the measured glucose flux for a given blood glucose concentration. Drift is computed by shifting the plotted glucose flux curve with respect to the blood glucose concentration curve along the glucose flux axis by a constant multiple of the time variable to achieve a best fit. The value of the constant multiple may be computed in many different ways. For example, experimental data taken from a given subject at given times under "baseline" conditions (i.e., the patient is fasting and the blood glucose level is therefore constant) may be subtracted from measured glucose flux data point by point during the oral glucose tolerance test at the same times for the same patient.

As another example, a linear fit (obtained, e.g., from a least squares linear regression) of the baseline data for a given patient may be subtracted from experimental data obtained during the oral glucose tolerance test. Measured glucose flux values can also be corrected without first obtaining baseline values. One approach is to estimate the value of drift time constant, adjust for drift based on the estimate, and determine the correlation between drift-corrected measured values and measured blood glucose values. The estimated drift time constant can then be increased or decreased, and the correlation recalculated, until an acceptable tolerance between measure glucose flux values and blood glucose values is achieved.

The drift time constant may also be computed by measuring a different physiological parameter, such as the electrical resistance of the patient's skin (which may change with time in the same manner as the glucose flux value drift) or a parameter that remains relatively constant over time, such as the pH of the patient's blood.

Finally, the slope and intercept of the relationship between the time and drift corrected values is computed using a linear best fit of the data. These steps may be performed by hand or by a suitably programmed processor or computer.

Other correlation variables and correlating relationships may be determined for other sample substances.

The sampled substance may be present in non-systemic amounts in the stratum corneum prior to application of the monitoring method and device. A time delay may therefore be provided between the start of the sampling and the time of analysis.

The method of this invention may be performed substantially continuously for an indefinite period of time. The method of the invention may also include the step of treating the patient in response to the determined (i.e., correlated) systemic concentration of the substance in the patient.

The collection reservoir/sampling chamber of the device of the invention can be in the form of (1) a single chamber with an electrode, which alternates polarity, with an indifferent counterelectrode which also alternates polarity, with the electrode in the sampling chamber acting as anode, cathode or both during the course of sampling, (2) two chambers in which the anode and cathode chambers are on alternate sites as the polarity alternates or (3) two or more chambers in which the polarity alternates during the treatment allowing for signal averaging between cathode and anode.

The collection reservoir/sampling chamber for receiving the sample of the target substance from the subject can be in the form of adhesive patch enclosing the electrode means. A wide variety of adhesives for patches are known in the iontophoresis art.

Figure 1A:
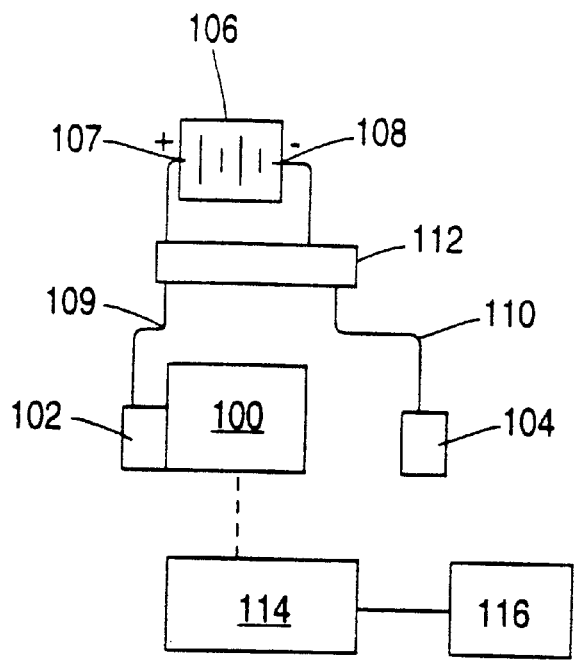
FIG. 1A is a block diagram of a substance monitoring device according to the invention.

FIG. 1A shows in block diagram form a monitor according to this invention. The monitor includes a collection reservoir 100 containing a collection medium. A pair of electrodes 102 and 104 connected to a power supply 106 having positive and negative connectors 107 and 108, respectively, via conductors 109 and 110 and a switch 112 provide current for transport of the sampled substance from a tissue surface into reservoir 100. The switch 112 may be controlled manually or by an automatic controller 113. An analyzer 114 associated with the monitor measures the substance concentration in collection reservoir 100 and computes a substance flux. A calibrator 116 correlates the computed substance flux with the patient's systemic concentration.

Figure 1B:
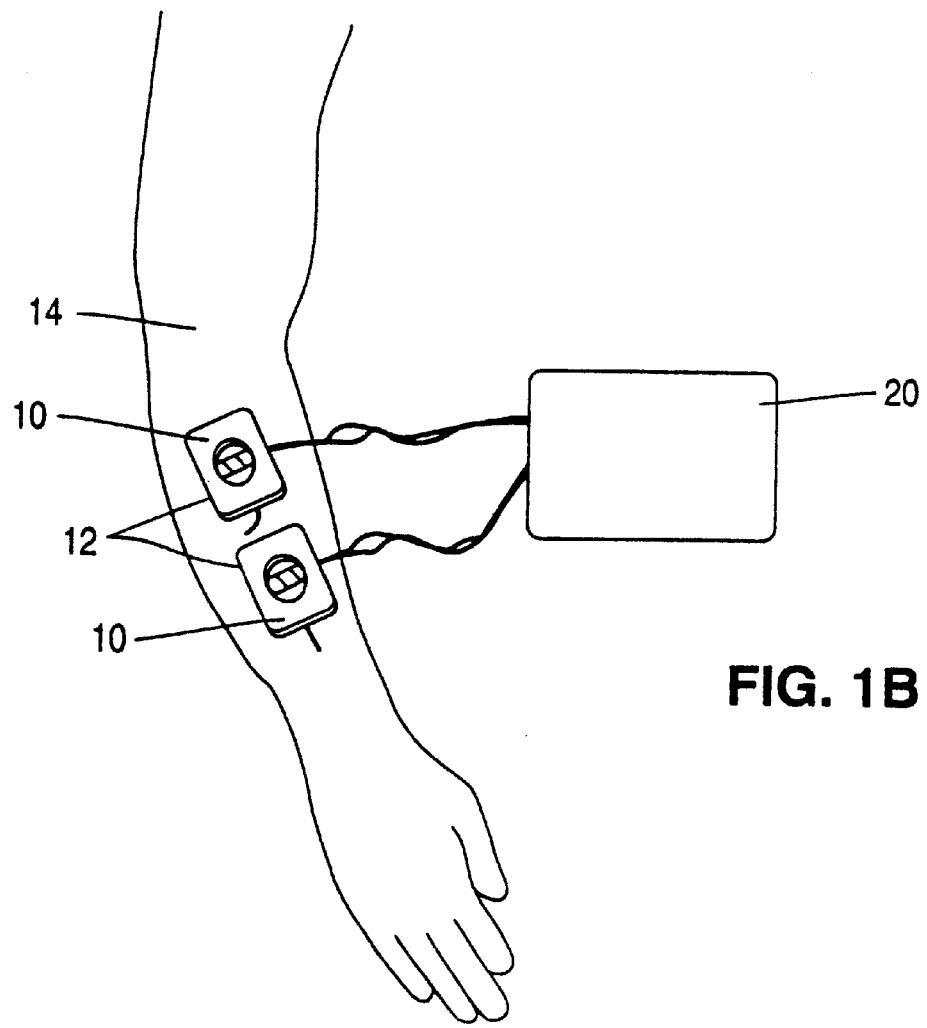
FIG. 1B shows an iontophoretic monitoring device useful for practicing this invention in place on a patient.
Figure 1C:
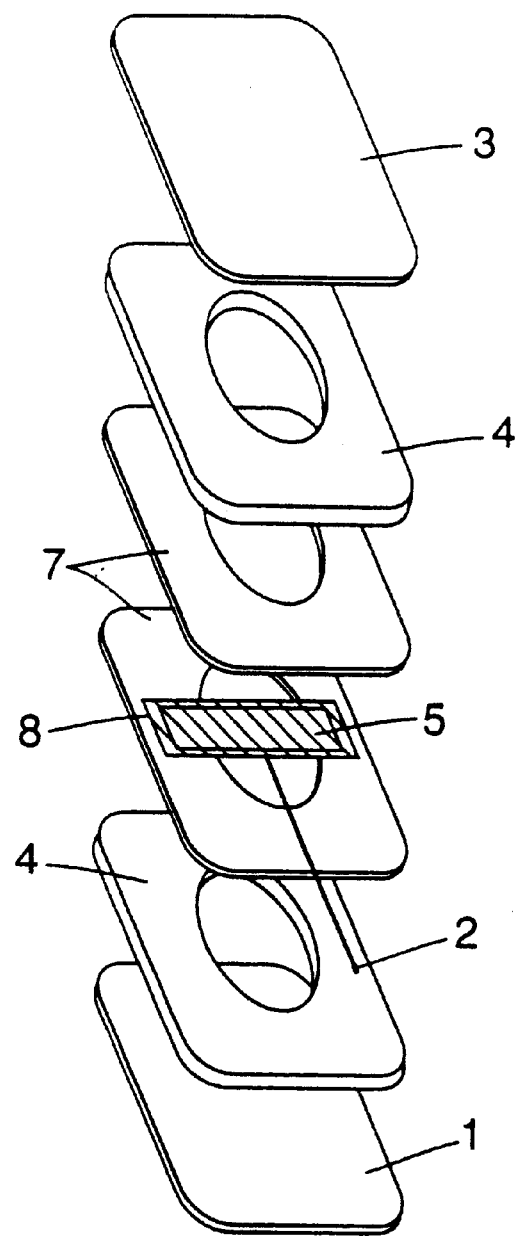
FIG. 1C is an exploded drawing of the electrode/collection reservoir assembly illustrating the various layers thereof.
Figure 1D:
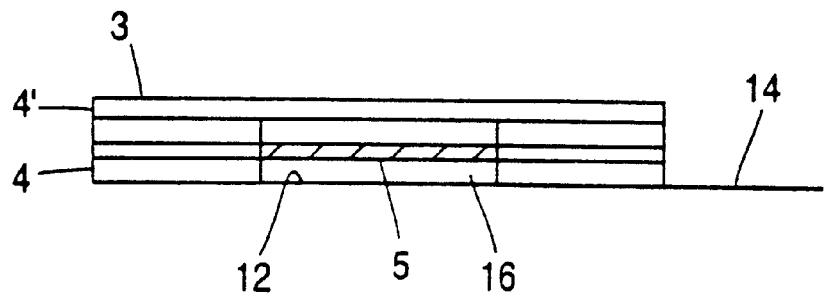
FIG. 1D is a cross-section of one of an electrode/reservoir assembly FIG. 1C.

FIGS. 1B–1D are drawings of a preferred device for practicing the method of this invention. As shown in FIG. 1B, two integral electrode/reservoir assemblies 10 are attached to collection sites 12 on a tissue surface 14 of a patient. The electrode/reservoir assemblies 10 are connected to a power supply 20.

FIG. 1C is an exploded view of the electrode/reservoir assembly 10. Element 1 is a release liner which is a protective layer for the adhesive of the skin contacting surface of the patch; element 2 is a sample port which can be a tube through which samples are removed; element 3 is the top layer, which can be a polymeric layer, which forms the upper housing for the collection reservoir/sample chamber and makes it possible to view the condition of the electrode as the treatment progresses; element 4 is a foam layer coated on one side with an adhesive top layer, which prevents contact of the electrode with the skin and serves as the walls of the collection reservoir/sample chamber; element 5 or 6 is an electrode which serves as either the cathode (i.e., electron donor) or the anode (i.e., electron receiver) depending on the polarity of the electrodes; element 7 is a transfer adhesive layer which holds the electrode 5 and the sample port 2 in place; and element 8 is a protective layer positioned between the electrode 5 and the skin to prevent the electrode from contacting the skin.

As illustrated, layers 4 and 7 each comprise part of the housing of the collection reservoir and allow for the collection reservoir to be open to the skin.

The release liner 1 is a protective layer for the adhesive of the skin contacting surface of the patch. This liner can be any suitable flexible material conventional known in the art. It should be strong enough not to be torn away by normal movement but easily removed by the application of some manual effort.

The sample port 2 can be a tube through which samples are removed.

The top layer 3 can be any flexible material conventionally known in the art, such as a polymeric layer, which forms the upper wall of the housing of the collection reservoir/sample chamber and is preferably transparent, which makes it possible to view the condition of the electrode as the treatment progresses. Any transparent polymeric material conventionally used as the top layer in transdermal patches can be used. Preferably, the top layer is made of polyester or preferably polyethylene.

The foam layer 4 is any medical grade foam coated on one side with an adhesive (foam tape) which prevents contact of the electrode with the skin and serves as the walls of the sample chamber. Any foam tape which is conventionally used in transdermal patches which is compatible with the tissue and material to be sampled can be used, preferably the foam tape is a closed-cell polyolefin foam coated on one side with an acrylate adhesive, such as 3M #9773.

The electrode 5 can be made of Ag/AgCl or any other electrode material. It is attached to the power source via electrical wires/leads.

The transfer adhesive layer 7 which is a transfer adhesive layer which holds the electrode and the sample port in place. The adhesive can be any adhesive conventionally known in the art which can hold the layers together with the electrodes between. For example, the transfer adhesive can be 3M Product # 1524, medical transfer tape.

The protective layer 8 is positioned between the electrode 5 and the skin to prevent the electrode from contacting the skin. The protective layer is a polyurethane film coated on one side with an adhesive layer which keeps it in contact with the electrodes. Any conventional adhesive which is compatible with the skin can be used. For example, the protective layer is an Acutek tape (Flexcon-Deraflex NRU 100 clear H566 spec 50K-9 (nylon reinforced cast polyurethane film coated with an acrylic adhesive).

FIG. 1D is a cross-section of one of an electrode/reservoir assembly 10 in place at the collection site 12. A collection reservoir/sampling chamber 16 is preferably filled with an electrically conductive medium/fluid. Any fluid which is capable of conducting electric current between the electrodes can be used. Suitable fluids include water, aqueous saline solutions and preferably aqueous buffered saline solutions having a pH in the range of from about 4 to about 9. A preferred fluid is an aqueous sodium bicarbonate buffered sodium chloride solution having a pH of from about pH 7 to about pH 9. Obviously, the fluid is one that is inert to the material desired to be sampled (i.e., glucose) and compatible with skin. The collection medium provides an electrical circuit connection between electrode 5 and the tissue surface.

Instead of the collection reservoir described above, a collection matrix may be provided, as in known in the art. Also, electrodes in direct contact with the skin may be used in place of the electrodes immersed in conductive fluid as described above. The electrodes may be placed at the collection site or adjacent to the collection site.

Preferably, power supply 20 comprises a means for reversing the polarity of the power source during the sampling, such as a manual or automatic programmable switch. One suitable power supply is the Iomed Phoresor2 iontophoretic power supply.

One of skill in the art can recognize that there is variation between subjects or even for a given subject and for use of different iontophoretic device designs, surface area, current density, and the like as to background (non-systemic) substance concentrations, time lag and drift. These can be determined by standard methods and the correlation of the data adjusted for background substance concentrations, time lag and drift for an individual and/or device.

In one embodiment the invention includes a substance monitor comprising:
  first and second substance sampling chambers each containing substance collection medium selected from the group consisting of water, saline solutions, buffer solutions, and polyols;
  a power supply means having a positive connector and a negative connector;
  conductors and a switch electrically connecting the first and second sampling chambers to the power supply means' positive connector and the power supply means' negative connector, the switch having a first position in which the first sampling chamber is electrically connected to the positive connector and the second sampling chamber is electrically connected to the negative connector and a second position in which the second sampling chamber is electrically connected to the positive connector and the first sampling chamber is electrically connected to the negative connector.

Preferably, the monitor is one in which the first and second sampling chambers each further comprises an electrode in electrical communication with the collection medium and with the power supply through a conductor and the switch.

The method of the invention is preferably one wherein the tissue surface is a stratum corneum surface of the patient's skin, the analysis step comprising the step of delaying the time between the applying step and the analyzing step to allow for depletion of non-systemic substance (glucose) in the stratum corneum.

The delaying step can comprise delaying performance of the analyzing step for about one hour after commencing the applying step.

The method of the invention preferably is one in which the collection reservoir contains a collection medium, the analyzing step comprising the step of extracting at least a portion of the collection medium form the collection reservoir.

The method of the invention can further comprise the step of providing correlation data between collection reservoir substance (glucose) levels and patient's blood substance (glucose) levels.

The method of the invention can also include the correlating step comprising calculating substance (glucose) flux from the collection site into the collection reservoir.

The method of the invention preferably comprises the method wherein the steps of placing the collection reservoir on a tissue surface, applying the electrical energy to the tissue, analyzing the collection reservoir for collected substance concentration, and correlating the analyzed substance concentration with systemic level are performed substantially continuously for about 2 hours to about 72 hours, preferably from about 16 hours to about 24 hours.

EXAMPLES

The following examples are provided to illustrate the invention but should not be regarded as limiting it in any way.

Example 1

Blood glucose monitoring experiments were performed in which a comparison was made between a standard iontophoretic protocol consisting of direct current (DC) between an anode site and a cathode site versus an iontophoretic protocol of this invention in which the electrodes act as both the anode and the cathode (alternating polarity, AP) during the course of extraction. Two iontophoretic extractions were performed simultaneously on human subjects, one using the standard (DC) protocol on the right arm and the other using the protocol of this invention (AP) on the left arm.

In these experiments, two adhesive sampling patches, each with Ag or AgCl electrodes inserted into the aqueous sampling chamber of the patches, were applied to each forearm. The iontophoretic patches had a collection surface area of 2.85 $cm^2$ per patch and a collection reservoir volume 0.4 mL per patch. The chambers were filled with 0.45% sodium chloride in water, U.S.P.

For the direct current or DC protocol (the standard protocol), a current of 0.32 $mA/cm^2$ was applied for about 15-minutes, followed by a 5-minute interval in which the saline was removed for analysis and then replaced with fresh saline. During the 5-minute rest period, blood glucose was measured by a standard finger prick (One Touch Basic, LifeScan, Milpitas, Calif.) method for comparison to extracted glucose. The 15-minute iontophoresis and 5-minute rest/sampling procedure was repeated over a period of 3 to 5 hours. The extract samples were analyzed by HPLC.

The method of this invention (alternating polarity, AP) was identical to the standard protocol, except that the polarity of the power supply was switched during each 5-minute rest period. In this way, the cathode chamber of one 5-minute period became the anode chamber of the next 5-minute period, and vise versa.

During the method, an oral glucose tolerance test was conducted on the non-diabetic subjects who had fasted prior to the experiment for 12 hours overnight. One hour into the test, 75 g of glucose was administered orally. Blood glucose levels typically increased from 80 to 150 mg/dL. The results of the test are set forth in FIGS. 2–5.

Figure 4:
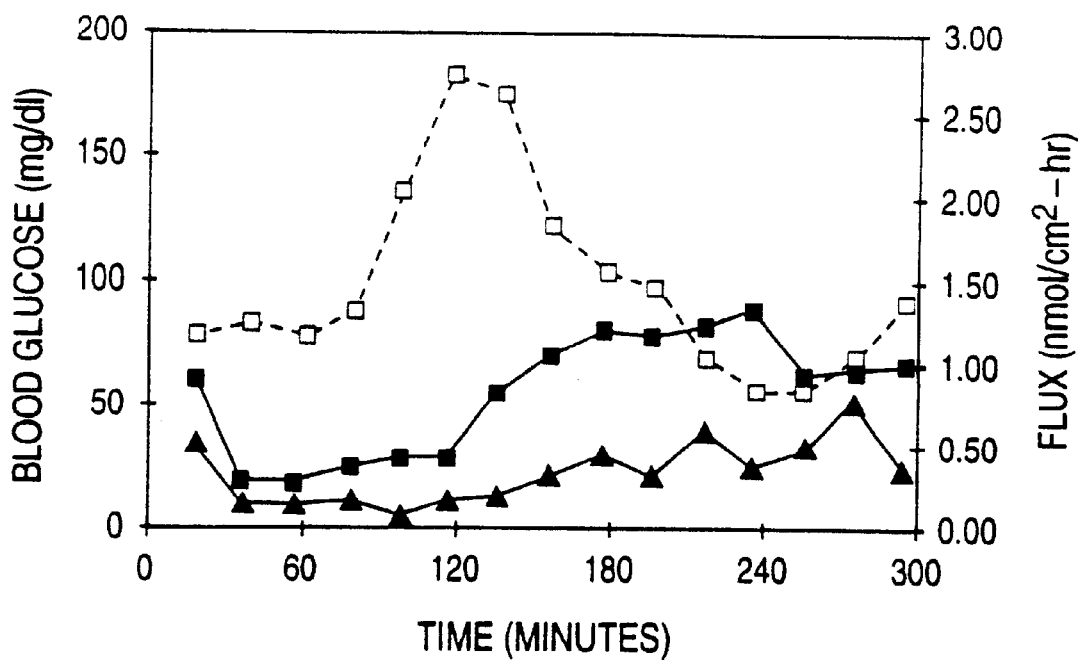
FIG. 4 is a graph of the results of a blood oral glucose tolerance glucose monitoring experiment on subject B, right arm, using a standard protocol.
Figure 5:
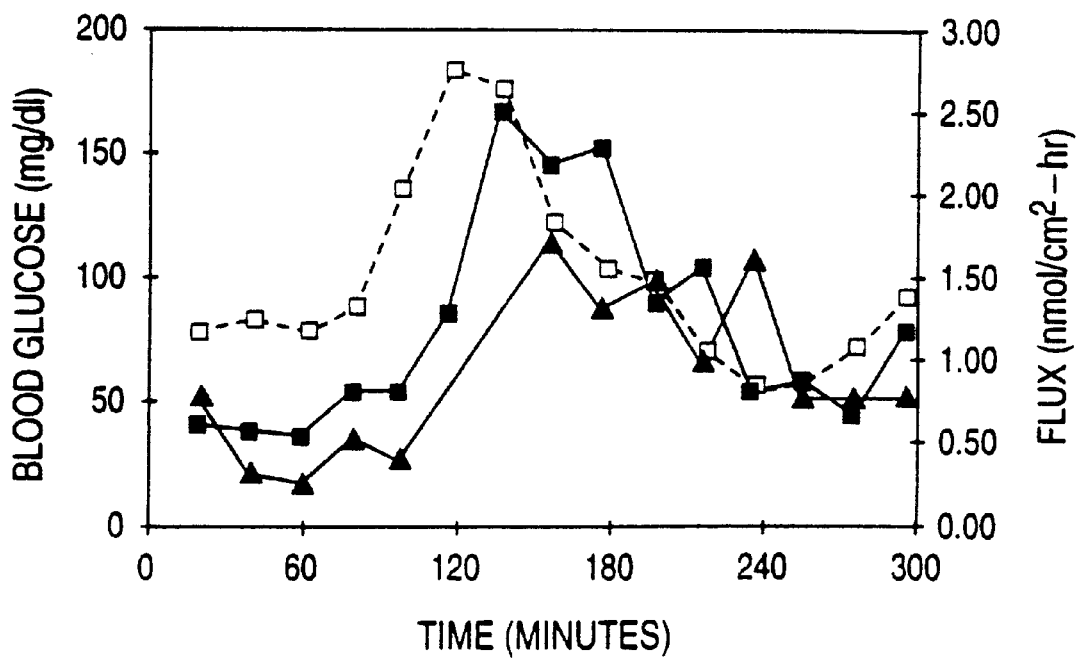
FIG. 5 is a graph of the results of a blood oral glucose tolerance glucose monitoring experiment on subject B, left arm, using an alternating protocol.

These figures are graphs comparing the results of the standard protocol and the alternating polarity method of the invention performed simultaneously on the same subject. FIGS. 2 and 4 show the standard (DC) method, which was performed on the right arms of subjects A and B, respectively, and FIGS. 3 and 5 show the alternating polarity method of the invention, which was performed on the left arms of subjects A and B, respectively. In each figure, blood glucose concentration in mg/dL is given versus time in minutes. The "x" is for blood glucose, solid triangle is for iontophoretic glucose at the anode, and the solid square is for iontophoretic glucose at the cathode.

As can be seen by comparing the FIGS. 2 and 4 with FIGS. 3 and 5, respectively, the alternating polarity method of the invention gave better correlation, particularly for the anode response.

The above results demonstrate the improvement in sampling profiles from alternating polarity, or the use one or more sampling electrodes that act, alternatively, as anode and cathode during a cycling period during the course of the extraction, as compared to the direct current (DC) standard mode of iontophoresis.

Example 2

Figure 6:
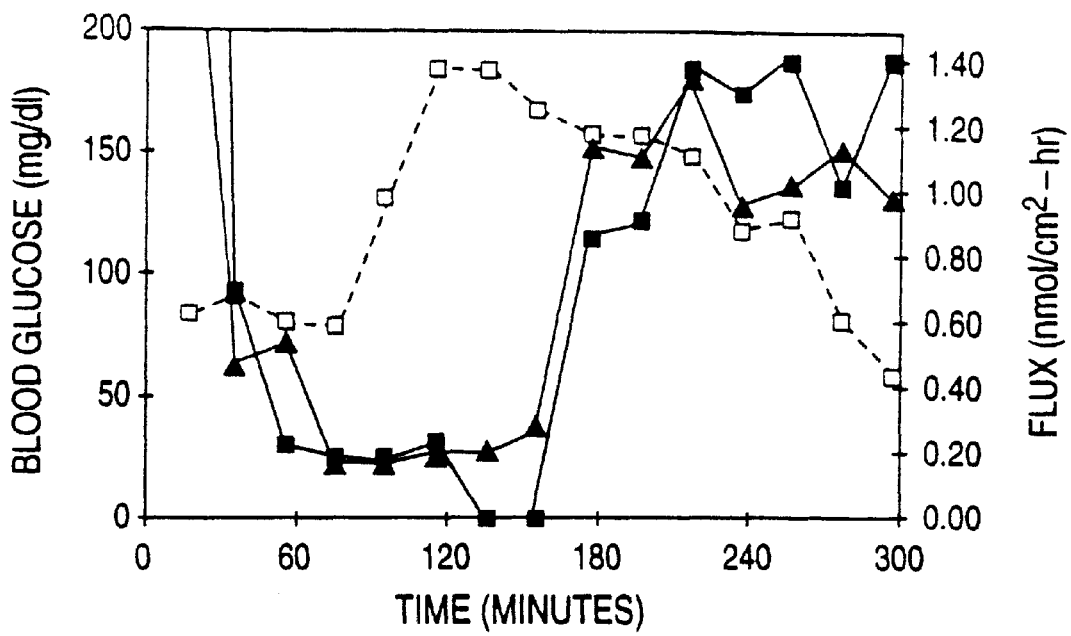
FIG. 6 is a graph of the results of a blood glucose monitoring experiment using several cycles of direct current and a cycle of alternating polarity.

A continuous iontophoretic extraction was conducted on subject C. Iontophoresis was administered and glucose was monitored as described in Example 1 above, with the following modification. The 15-minute extraction, 5-minute rest period sampling procedure was applied DC for 8 sampling periods. On the 9th sample period, the current was switched to an alternating polarity protocol of a switch every 15-minutes. The results are set forth in FIG. 6. There was a sharp and dramatic increase in flux as the protocol was switched from direct current to alternating polarity.

Example 3

The following are results of tests in which the data from the alternating polarity protocol is corrected for time lag and/or drift as discussed below.

A continuous iontophoretic extraction was conducted on subject A as in FIG. 2, but in a protocol in which the subject had fasted 12 hours overnight prior to the start of the experiment and during the experiment (no oral glucose tolerance test). Iontophoresis was administered using the alternating polarity method of this invention and glucose was monitored as described in Example 1 above. The results are shown in FIG. 7.

Figure 7:
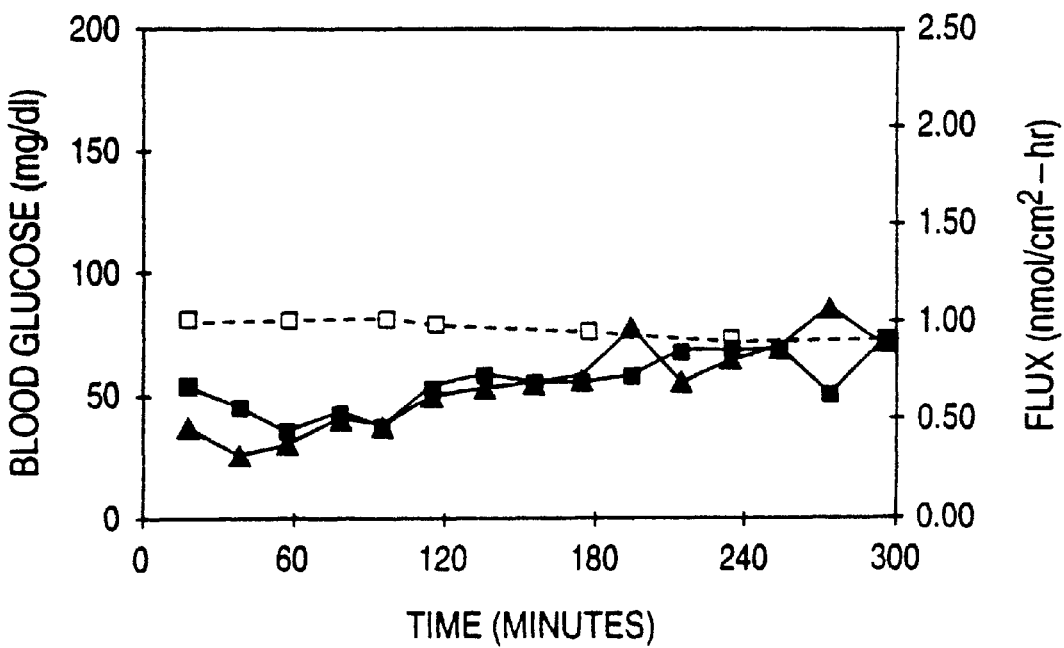
FIG. 7 is the results of a blood glucose monitoring experiment with the subject A of FIG. 3, under fasted conditions.

FIG. 7 demonstrates that there was a drift in the anode and cathode fluxes for subject A using alternating polarity.

Figure 8:
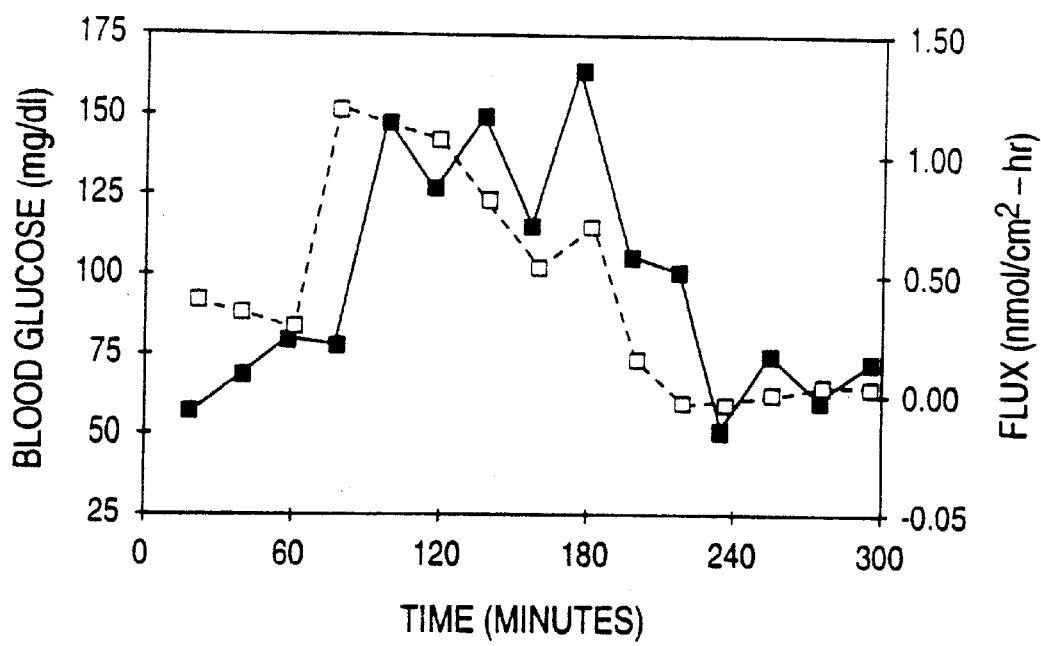
FIG. 8 is a graph of the results of a blood glucose monitoring experiment with the subject A of FIG. 3, left arm, compensating for drift at the cathode.

FIG. 8 is a graph of the results of a blood glucose monitoring as shown in FIG. 3 of subject A, but with the flux values for the cathode in FIG. 7 subtracted from the flux values for the cathode in FIG. 3.

Figure 9:
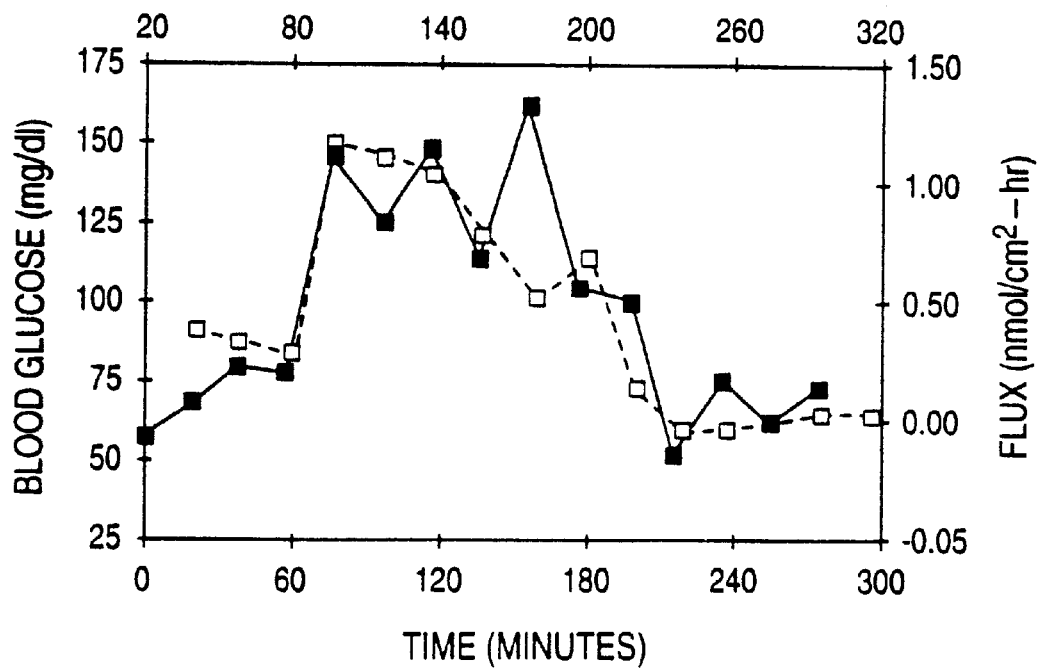
FIG. 9 is a graph of the results of a blood glucose monitoring experiment with the subject A of FIG. 3 compensating for time lag and drift at the cathode.

FIG. 9 is a graph of the results of a blood glucose monitoring as shown in FIG. 3 of subject A, but with the cathode flux adjusted for a 20 minute time lag and the drift as in FIG. 8.

Figure 10:
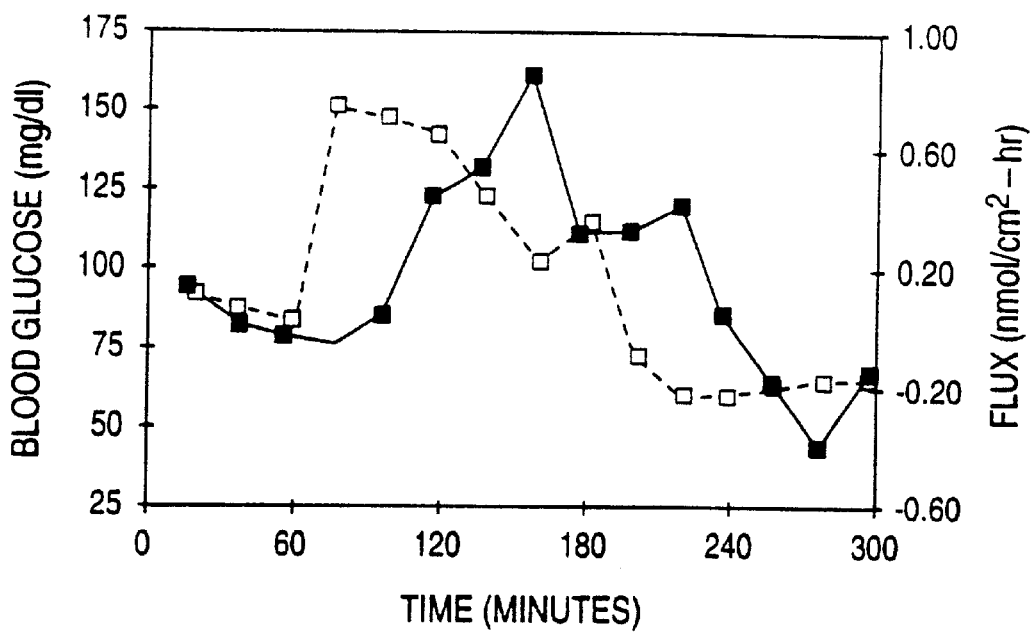
FIG. 10 is a graph of the results of a blood glucose monitoring experiment with the subject A of FIG. 3 compensating for drift at the anode.

FIG. 10 is a graph of the results of a blood glucose monitoring as shown in FIG. 3 of subject A, but with the flux values for the anode in FIG. 7 subtracted from the flux values for the anode in FIG. 3.

Figure 11:
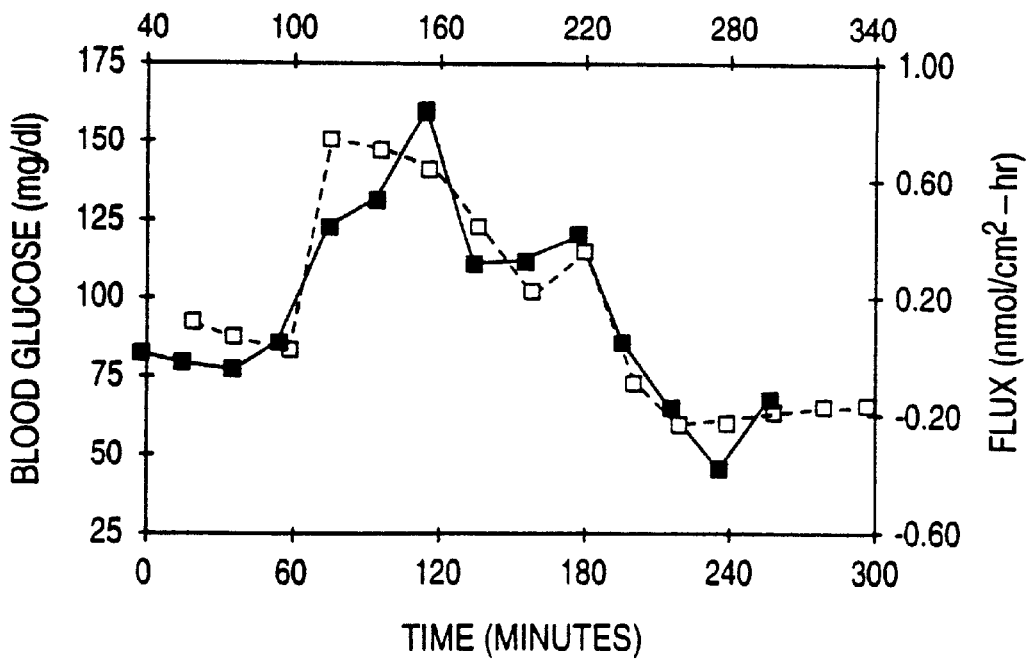
FIG. 11 is a graph of the results of a blood glucose monitoring experiment with the subject A of FIG. 3 compensating for time lag and drift at the anode.

FIG. 11 is a graph of the results of a blood glucose monitoring as shown in FIG. 3 of subject A, but with the anode flux adjusted for a 40 minute time lag and the drift as in FIG. 10.

Figure 12:
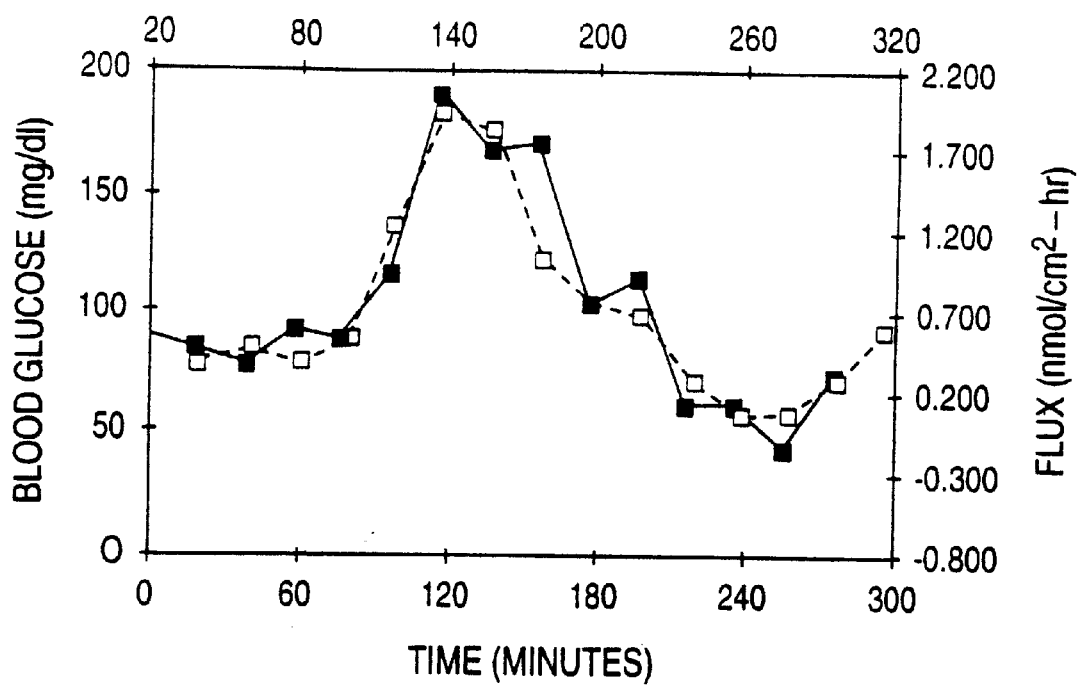
FIG. 12 is a graph of the results of a blood glucose monitoring experiment with the subject B of FIG. 5, left arm, compensating for time lag and drift at the cathode.

FIG. 12 is a graph of the results of a blood glucose monitoring as shown in FIG. 5 of subject B, but with the cathode flux adjusted for a 20 minute time lag and an empirically fitted linear drift.

Figure 13:
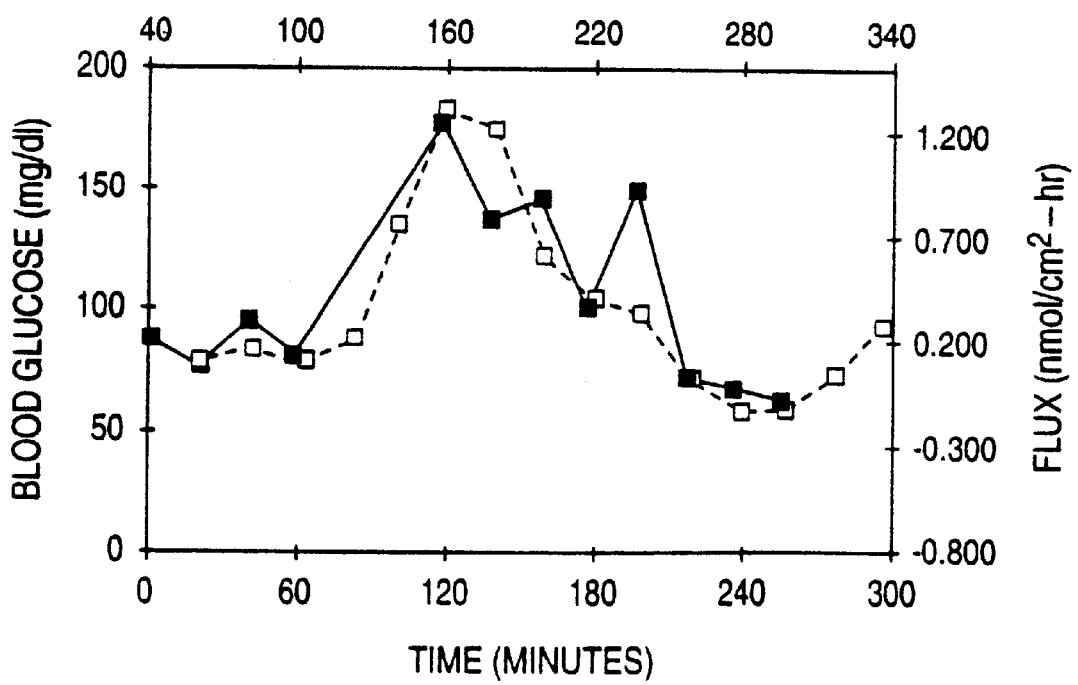
FIG. 13 is a graph of the results of a blood glucose monitoring experiment with the subject B of FIG. 5, left arm, compensating for time lag and drift at the anode.

FIG. 13 is a graph of the results of a blood glucose monitoring as shown in FIG. 5 of subject B, but with the anode flux adjusted for a 40 minute time lag and an empirically fitted linear drift.

Example 4

Two iontophoretic extractions were performed simultaneously on subject D, one using the standard (DC) protocol on the right arm and the other using the protocol of this invention (AP) on the left arm. Iontophoresis was administered and glucose was monitored as described in Example 1 above. The results of the test are set forth in FIGS. 14 and 15.

In FIG. 15, Subject D showed sharp oscillation in the iontophoretically extracted glucose at the cathode as the physical site of extraction was switched from one extraction site on the forearm to the other during the alternating polarity protocol.

FIG. 14 demonstrates that the standard DC protocol did not show this oscillation.

In total, 12 normal subjects were tested as in Examples 1 and 4. The results are summarized in Table 1 below.

TABLE 1

|  | Direct Current | | Alternating Polarity | |
| --- | --- | --- | --- | --- |
|  | Cathode | Anode | Cathode | Anode |
| Good tracking | 0 | 5* | 7 | 4 |
| Oscillation | 0 | 0 | 5 | 6 |
| Long Lag (>60 min) | 5 | 1 | 0 | 2 |
| No response | 7 | 6 | 0 | 0 |
| TOTAL | 12 | 12 | 12 | 12 |

Good = tracking with drift = $r^2 \geq 0.5$, lag $\leq$ 40 min
Long lag = $r^2 \geq 0.5$, lag $\geq$ 60 min
Oscillation = qualitative tracking with oscillation ($r^2 \geq 0.5$, lag $\leq$ 40 min)
No response = $r^2 \leq 0.5$
*Anode tracking, but low magnitude of flux Example 5

A continuous iontophoretic extraction was conducted on one arm of subject B, as in FIGS. 4 and 5, except with a polarity switch every 7.5 minutes instead of every 15 minutes. Iontophoresis was administered and glucose was monitored as described in Example 1 above, with the following modification. Halfway through the 15-minute extraction period, the polarity was switched while the saline solution remained in the sample chambers. The sample was removed at the end of the 15-minute cycle. In this way, each electrode acts as the cathode for 7.5 minutes and the anode for 7.5 minutes. This method was performed simultaneously on the other arm with the 15-minute alternating polarity protocol as described in Example 1 to the same subject B. The results are set forth in FIGS. 16 and 17.

FIG. 17 shows the oscillatory behavior, similar to that observed in Example 4, for the 15-minute alternating polarity protocol.

FIG. 16 shows that the oscillatory behavior is smoothed out by alternating the polarity every 7.5 minutes rather than every 15 minutes. The 7.5-minute protocol administered to each site an equal period of anode and cathode extraction. The correlation of extracted and blood glucose was thereby improved. This demonstrates that one or more electrodes can act as anode, cathode, or both during the course of the experiment.

Example 6

Two iontophoretic extractions using a modified buffer solution were performed simultaneously on same subject A as in FIGS. 2 and 3, one extraction using the standard (DC) protocol on the right arm and the other using the protocol of this invention (AP) on the left arm. Iontophoresis was administered and glucose was monitored as described in Example 1 above, with the following modification. Sodium bicarbonate buffer solution, 5% U.S.P, pH 7–9, mixed in a 1:9 ratio with 0.45% sodium chloride U.S.P. was used as the receiver solution instead of 0.45% sodium chloride. The results are set forth in FIGS. 18 and 19.

FIG. 18 demonstrates the dramatic enhancement in flux at the cathode for a direct current protocol using pH 8.2 sodium bicarbonate buffered saline solution compared to FIG. 2 for the same Subject B using 0.45% sodium chloride solution.

FIG. 19 demonstrates the dramatic enhancement of flux at the cathode for the alternating polarity protocol using pH 8.2 sodium bicarbonate buffered saline solution compared to FIG. 3 for the same Subject B using 0.45% sodium chloride solution. Further, a comparison of FIGS. 18 and 19 indicates that there was enhanced anode extraction for the sodium bicarbonate solution in the alternating polarity method compared to the direct current method.

What is claimed is:

1. A substance monitoring device comprising
   a transdermal sampling system comprising (i) a first sampling chamber for receiving a sample comprising said substance or substance metabolite, wherein the first sampling chamber comprises a first electrode that is connectable with an electrical power supply, and (ii) a second electrode that is connectable with said power supply;
   means for reversing polarity between the first electrode and the second electrode, wherein the first electrode functions as both an anode and a cathode during iontophoretic sampling;
   means for analyzing a concentration or amount of the substance or substance metabolite received in the first sampling chamber, and
   a programed processor for correlating said concentration or amount with a blood substance level.

2. The device of claim 1, wherein said second electrode comprises an indifferent counter electrode that also alternates polarity.

3. The device of claim 1, wherein said transdermal system further comprises a second sampling chamber, said second sampling chamber comprising said second electrode, wherein said second electrode alternates function as both an anode and a cathode during iontophoretic sampling.

4. The device of claim 3, further comprising
   means for analyzing a concentration or amount of a substance or a substance metabolite received in the second sampling chamber.

5. The device of claim 4, wherein said programmed processor provides correlation data between a substance level, in said first sampling chamber and said second sampling chamber, and blood substance levels.

6. The device of claim 3, wherein each sampling chamber comprises an Ag/AgCl electrode.

7. The device of claim 6, wherein each sampling chamber comprises a collection medium.

8. The device of claim 1, wherein said reversing of polarity is performed at a frequency comprising about 1 cycle per 20 seconds to about 1 cycle per 4 hours.

9. The device of claim 1, wherein said reversing of polarity is performed at a frequency comprising about 1 cycle per 20 seconds to about 1 cycle per 2 hours.

10. The device of claim 1, wherein said reversing of polarity is performed at a frequency comprising about 1 cycle per minute to about 1 cycle per 2 hours.

11. The device of claim 1, wherein said reversing of polarity is preformed at a frequency comprising about 1 cycle per 10 minutes to about 1 cycle per hour.

12. The device of claim 1, wherein said reversing of polarity is performed at a frequency comprising about 1 cycle per half hour.

13. The device of claim 1, wherein the first sampling chamber comprises an Ag/AgCl electrode.

14. The device of claim 13, wherein the first sampling chamber comprises a collection medium.

15. The device of claim 1, wherein said means for reversing polarity comprises a switch.

16. The device of claim 1, further comprising an electrical power supply.

17. The device of claim 1, wherein said sample comprises glucose.

18. The device of claim 1, wherein said sample comprises more than one substance.

19. A substance sampling device, comprising
   first and second substance sampling chambers for receiving a sample comprising said substance or a substance metabolite, each sampling chamber comprising an electrically conductive collection medium;
   a switch (i) connectable to a power supply positive connector and a power supply negative connector, and (ii) connected to the collection medium in said first sampling chamber by a first conductor, and connected to the collection medium in said second sampling chamber by a second conductor, wherein the switch comprises a first position such that when the first sampling chamber is electrically connected to the positive connector, the second sampling chamber is electrically connected to the negative connector, and a second position such that when the second sampling chamber is electrically connected to the positive connector, the first sampling chamber is electrically connected to the negative connector, and
   means for analyzing a concentration or amount of a substance or a substance metabolite received in said first sampling chamber.

20. The substance sampling device of claim 19, wherein (i) the first sampling chamber further comprises an electrode in contact with the collection medium and said first conductor, and (ii) the second sampling chamber further comprises an electrode in contact with the collection medium and said second conductor.

21. The substance sampling device of claim 20, wherein each sampling chamber comprises an Ag/AgCl electrode.

22. The substance sampling device of claim 19, wherein the electrically conductive collection medium is selected from the group consisting of saline solutions, buffer solutions, and polyols.

23. The substance sampling device of claim 19, further comprising
means for analyzing a concentration or amount of a substance or a substance metabolite received in said second sampling chamber.

24. The substance sampling device of claim 23, further comprising a programmed processor for providing correlation data between sampling chamber substance level and blood substance levels.

25. The substance sampling device of claim 19, wherein switching from said first position to said second position is performed at a frequency comprising about 1 cycle per 20 seconds to about 1 cycle per 4 hours.

26. The substance sampling device of claim 19, wherein switching from said first position to said second position is performed at frequency comprising about 1 cycle per 20 seconds to about 1 cycle per 2 hours.

27. The substance sampling device of claim 19, wherein switching from said first position to said second position is performed at a frequency comprising about 1 cycle per minute to about 1 cycle per 2 hours.

28. The substance sampling device of claim 19, wherein switching from said first position to said second position is performed at a frequency comprising about 1 cycle per 10 minutes to about 1 cycle per hour.

29. The substance sampling device of claim 19, wherein switching from said first position to said second position is performed at a frequency comprising about 1 cycle per half hour.

30. The substance sampling device of claim 19, further comprising an electrical power supply.

31. The substance sampling device of claim 19, wherein said sample comprises glucose.

32. The substance sampling device of claim 19, wherein said sample comprises more than one substance.

* * * * *

UNITED STATES PATENT AND TRADEMARK OFFICE
CERTIFICATE OF CORRECTION

PATENT NO.    : 6,687,522 B2
DATED         : February 3, 2004
INVENTOR(S)   : Janet Tamada It is certified that error appears in the above-identified patent and that said Letters Patent is hereby corrected as shown below:

<u>Title page,</u>
Item [54], Title "DEVICE FOR SAMPLE OF SUBSTRANCES USING ALTERNATING POLARITY" should read -- DEVICES FOR SAMPLING OF SUBSTANCES USING ALTERNATING POLARITY --;

<u>Column 16,</u>
Line 17, "cycle per2 hours." should read -- cycle per 2 hours. --;

<u>Column 17,</u>
Line 18, "performed at frequency" should read -- performed at a frequency --.

Signed and Sealed this

Thirteenth Day of April, 2004

JON W. DUDAS
*Acting Director of the United States Patent and Trademark Office*